United States Patent [19]

Vishnupad et al.

[11] Patent Number: 4,980,084

[45] Date of Patent: Dec. 25, 1990

[54] WATER RINSABLE PETROLEUM JELLY COMPOSITIONS

[75] Inventors: Mohan Vishnupad, Monroe; Jose E. Ramirez, Trumbull; Thomas M. Deppert, Waterbury, all of Conn.

[73] Assignee: Chesebrough-Pond's USA Co., Division of CONOPCO, INC., Greenwich, Conn.

[21] Appl. No.: 253,446

[22] Filed: Oct. 5, 1988

Related U.S. Application Data

[63] Continuation of Ser. No. 941,131, Dec. 12, 1986, abandoned, which is a continuation-in-part of Ser. No. 774,727, Sep. 11, 1985, Pat. No. 4,690,774, and a continuation-in-part of Ser. No. 774,728, Sep. 11, 1985, abandoned.

[51] Int. Cl.$^5$ .............................................. B01J 13/00
[52] U.S. Cl. ................................... 252/309; 252/314; 514/939; 514/941; 514/942; 514/943
[58] Field of Search ............... 252/309; 514/939, 941, 514/942, 943

[56] References Cited

U.S. PATENT DOCUMENTS

| | | | |
|---|---|---|---|
| 2,617,754 | 11/1952 | Neely | 424/63 |
| 3,228,842 | 1/1966 | Markland et al. | 424/70 |
| 3,489,690 | 1/1970 | Lachampt et al. | 252/308 |
| 3,852,475 | 12/1974 | Tarangul | 514/778 |
| 3,957,971 | 5/1976 | Oleniacz | 252/DIG. 13 |
| 4,035,514 | 7/1977 | Davis | 514/786 |
| 4,151,304 | 4/1979 | Evans | 514/942 X |
| 4,216,201 | 8/1980 | Calvo | 424/63 |
| 4,407,824 | 10/1983 | Eckert | 514/555 |

FOREIGN PATENT DOCUMENTS

| | | |
|---|---|---|
| 1127039 | 7/1982 | Canada . |
| 009404 | 9/1979 | European Pat. Off. . |
| 0103910 | 6/1983 | European Pat. Off. . |
| 0216557 | 9/1986 | European Pat. Off. . |
| 0047804 | 9/1990 | European Pat. Off. . |

OTHER PUBLICATIONS

Chemical Abstracts, vol. 95, No. 6, Sep. 1981, p. 342.
Household & Personal Products Industry, vol. 49, No. 3, Mar., 1976.
Soap, Perfumery and Cosmetics, vol. 49, No. 3, p. 91, Table 12.
Flick: *Cosmetic and Toiletry Formulations*, Noyes Publications, Park Ridge, N.J., 1984, pp. 225 and 226.

*Primary Examiner*—Richard D. Lovering
*Attorney, Agent, or Firm*—Melvin H. Kurtz

[57] ABSTRACT

A water rinsable petroleum jelly formulation, which is a water-in-oil preferably translucent emulsion, is described which comprises an aqueous phase containing a humectant, as a preferable component, and a surface active detergent effective to confer rinsable characteristics on the emulsion, an oil phase comprising a petroleum jelly component, and a water-in-oil emulsifying agent.

18 Claims, No Drawings

WATER RINSABLE PETROLEUM JELLY COMPOSITIONS

This application is a continuation of Ser. No. 941,131, filed Dec. 12, 1986 and now abandoned, which is a continuation-in-part of Ser. No. 774,727 filed Sept. 11, 1985, now U.S. Pat. No. 4,690,774, and Ser. No. 774,728 filed Sept. 11, 1985 and now abandoned.

BACKGROUND OF THE PRESENT INVENTION

1. Field of the Invention

The present invention relates of petroleum jelly compositions (water-in-oil emulsions) which are easily rinsable in water.

2. Description of the Prior Art

It is taught in U.S. Patent No. 3,852,475 that the inclusion of hydrophobic starch in topical compositions containing solid petroleum jelly reduces the greasy appearance and feel normally associated with such compositions as well as reducing the resistance of the compositions to washing with cold water soap and detergent compositions. The compositions that are shown in this patent contain no aqueous phase, are anhydrous formulations and, therefore, are not emulsions. Similarly, U.S. Patent No. 4,035,514 indicates that petroleum jelly containing up to 30% by weight of a combination dispersing agent comprising cetyl alcohol, lanolin alcohols and alkoxylated fatty acid esters of sorbitol can be dispersed in water without the use of additional soaps or detergents. Once again, this reference relates to petroleum jelly compositions which do not contain a water phase and are thus anhydrous in nature. The compositions shown in this patent are merely designed to be dispersed in water and consist of an oil phase in combination with the dispersing agent only.

U.S. Pat. No. 3,489,690 describes water-in-oil emulsions which can contain petroleum jelly (e.g., from 13%- 32%, by weight), but these emulsions are water resistant and removable only by using a cleansing cream or lotion.

Transparent mineral oil-Water gels comprising oil and water soluble emulsifier ®are covered in U.S Pat. No. 3,228,842. Although these are described as being water rinsable, this patent fails to contain any incentive to use petroleum jelly in place of, or even with, the mineral oil component since it clearly indicates that mineral oil offers "unique and distinctive" advantages, in part, by lacking the "tackiness typical of some other oils and synthetic oils". The compositions described in the '842 patent differ from the compositions of the present invention: they are oil-in-water microemulsions rather than being a water-in-oil gel emulsion; they rely upon oil and water soluble ethoxylated surfactants, rather than the present compositions which use a detergent/emulsifier combination having certain desired characteristics; and they fail to contain any petroleum jelly component and, in fact, teach aWay from use of such a component.

Significantly, U.S. Patent No. 2,617,754 also appears to provide, if anything, a negative suggestion of the present invention, which is to be described in greater detail below. Since it indicates (at Col. 3, lines 11-16) that mixtures of mineral oil and "mineral wax" (a term it uses for petroleum jelly), even if combined with emulsifiers, are so strongly hydrophobic in nature that, when spread on the face or hands, they are not removable by water alone. More recently, page 225 of Cosmetic and Toiletry Formulations by E. W. Flick lists a petrolatum-/emulsifier cream which is indicated as being "oily" since "it is not dispersible in water".

DESCRIPTION OF RELATED DEVELOPMENTS

Certain high oil-containing anhydrous foamable compositions are described in copending U.S. Serial No. 774,728, filed September 11, 1985 and now abandoned, which comprise a petroleum jelly oil component in combination with a mild detergent component of such nature and in such amount for imparting foaming characteristics When the composition is subsequently combined with water. The anhydrous base compositions shown in this copending application do not contain a water phase.

Certain novel translucent Water-in-oil emulsions containing petroleum jelly are described in copending U.S. Ser. No. 774,727, filed September 11, 1985 and now U.S. Pat. No. 4,690,774. These water-in-oil emulsions have the same general appearance and feel as petroleum jelly. They comprise an aqueous phase containing a humectant, an oil phase comprising petroleum jelly or petroleum jelly modified with mineral oil, and a water-in-oil emulsifying agent. These water-in-oil emulsions are, however, not readily rinsable with water and do not contain a surface active detergent in their aqueous phase.

SUMMARY OF THE PRESENT INVENTION

The present invention is a readily water rinsable petroleum jelly water-in-oil emulsion which comprises an aqueous phase containing a humectant and a surface active detergent effective to confer rinsable characteristics on the emulsion, an oil phase comprising petroleum jelly, and a water-in-oil emulsifying agent. In its preferred embodiment, the compositions of the present invention are translucent due to the aqueous and oil phases each having a refractive index which is essentially in the same range.

DETAILED DESCRIPTION OF THE PRESENT INVENTION

The oil phase of the compositions of the present invention comprise petroleum jelly either in neat or modified form as the petroleum jelly component. Modified forms of petroleum jelly include those compositions where some (e.g., a minor portion) of the petroleum j®lly has been replaced by mineral oil. The petroleum jelly that is intended for us ®in a preferred embodiment is a purified mixture of semi-solid hydrocarbons obtained from petroleum, chiefly of the methane series having a white to faintly yellowish color, a density of from about 0.820–0.865, a melting point of from about 38-54° C. and a refractive index of 1.460–1.474. The amount of the oil phase in the present emulsions can range anywhere from about 40% to about 70% by weight of the total weight of the emulsion. In the compositions of the present invention, the amount of either petroleum jelly or of petroleum jelly and mineral oil predominates over the amount of any other ingredient.

The aqueous phase of the present invention comprises water, a humectant, and a surface active detergent which is effective to confer rinsable characteristics on the composition of the present invention as essential ingredients. Generally speaking, the weight percentage of the aqueous phase can range anywhere from about 3D to about 60% by weight. The amount of water itself can comprise about 6% to about 20% by weight of the entire composition.

A preferred humectant for use in preferred embodiments of the present invention is the sodium salt of pyrolidone carboxylic acid. Such compositions are commercially available and can be formed by heating glutamic acid monoalkali metal salts with plutamic acid in water under high pressures followed by neutralization of the reaction liquids if needed. If desired, this type of humectant can be combined with further amounts of such humectants as glycerine, propylene glycol, sorbitol, and sucrose. Generally speaking, the amount of secondary humectant can preferably range up to about 50% by weight of the total humectant amount in order to avoid possibly compromising the preferred homogeneity, texture and nontacky characteristics of preferred embodiments of the present invention.

The surface active detergent which is used in the present invention is one which confers rinsable characteristics upon the resulting composition. Representative surface active detergents which can be used include the amido sulfonates (N-acyl-N-alkyl-taurates), and the 2-sulfoethyl esters of fatty acids (acyl isethionates). The alkali metal alkyl sulfates (e.g., sodium lauryl sulfate), the alkali metal alkyl sulfoacetates (e.g., sodium lauryl sulfoacetate), the alkali metal sulfosuccinate esters of modified alkanolamines (e.g., available under the trademark MONAMATE CPA I00 where the alkali metal cation is sodium and a coconut acid radical is attached to the carboxy group), and the dialkyl alkali sulfosuccinates (e.g., dioctyl sodium sulfosuccinate). A particularly preferred surface active detergent in view of its mildness is sodium cocoyl isethionate. Another is sodium lauryl sulfoacetate.

Generally speaking, the amount of humectant can range anywhere from about 10% to about 20% by weight of the entire composition with the amount of surface active detergent being present at from about 2% to about 8% by weight of the composition.

It has been found that surface active detergents containing the group $SO_3^-A^+$, where A is alkali metal such as sodium, have good compatibility with a pyrrolidone carboxylic acid humectant (e.g., the sodium of such an acid).

Another essential component of the present compositions is a water-in-oil emulsifying agent. Examples of suitable water-in-oil emulsifiers that can be used include the following: polyglycerol - 4 cocoate, polyglycerol - I0 decaoleate, polyglycerol I0 decalinoleate, polyglycerol - 2 diisostearate, polyglycerol - 3 diisostearate, polyglycerol - 6 dioleate, polyglycerol - 6 distearate, polyglycerol - 4 isostearate, polyglycerol -3 oleate, polyglycerol - 4 oleate, polyglycerol - 2 sesquiisostearate, polyglycerol - 2 sesquioleate, polyglycerolIII - stearate, polyglycerol - 4 stearate, polyglycerol - 8 stearate, polyglycerol 10 tetraoleate and polyglycerol - 2 tetraoleate. Generally speaking the amount of such emulsifying agent can be present at from about 0.1% to about 5 % by weight of the compositions of the present invention.

In addition to the foregoing essential components, the compositions of the present invention can include various optional additives to enhance the commercial utility of the compositions of the present invention. Included within possible optional additives are the following: preservatives (such as methylparaben and propylparaben); coloring agents or dyes; inert fillers; medicinal agents; and the like.

In producing the water-in-oil emulsions of this invention, which is preferably translucent, the following general procedure which may be used includes the employment of conventional preservatives Which protect against spoilage by contaminating microorganisms.

The oil phase is formed by combining the appropriate amounts of petroleum jelly and the like (e.g., petroleum jelly and mineral oil) into an appropriate oil-phase kettle. With agitation the mixture is heated until a clear liquid is obtained. Any suitable oil-soluble preservative (e.g., propylparaben) can be added and mixed until dissolved. To the clear liquid can then be added a suitable amount of emulsifier with agitation.

The water phase can be prepared in a suitable water-phase kettle by first adding to the kettle the appropriate amount of water. An appropriate water-soluble preservative (e.g., methylparaben) can be added with agitation. A suitable amount of humectant and surface-active detergent can be added into the water phase and agitation can be continued until clear solution is obtained.

An appropriate dye can be added to the water phase. The water, humectant, detergent, dye and any other components of the water phase should be of such nature and in such amounts that the resulting water phase of the emulsion to be produced will preferably have a refractive index close to that of petroleum jelly, i.e., I 4 to i.8, most preferably 1.45 to 1.48.

The water phase can be slowly transferred to the oil-phase kettle with proper high speed agitation, preferably using a side scraper with a homo-head attached to the kettle.

After addition of the water phase, mixing can be continued for a suitable length of time (e.g., 10-15 minutes) to form a uniform Water-in-oil emulsion. The resulting emulsion is then homogenized at 70° C. for 20-30 minutes while controlling aeration during homogenizing. After the homogenization is complete, the batch can be cooled to 50° C., using slow cooling (to avoid undesired solidification of the material on the walls of the vessel) by gradually adding water to the jacket.

The Examples which follow set forth certain embodiments of the present invention.

EXAMPLE 1

This illustrates a preferred formulation in accordance with the present invention where a combination of humectants was used to form a rinsable. water-in-oil, translucent emulsion.

| Ingredient | Weight Percent |
| --- | --- |
| Oil Phase Additive | |
| Petroleum Jelly | 50.00 |
| Mineral Oil (200 SUS) | 9.97 |
| Folyglycerol isostearate emulsifier (WITCONOL 18L brand) | 1.00 |
| Sodium cocoyl isethionate detergent (JORDAPON CP brand) | 4.00 |
| Propylparaben | 0.10 |
| Water Phase Additive | |
| Solution (50%) of sodium pyrrolidone carboxylic acid | 30.00 |
| Sugar | 4.80 |
| Methylparaben | 0.10 |
| Color Additive | |
| Yellow No. 10 coloring (0.5%) | 0.03 |

The ingredients in the oil phase, with the exception of the isethionate, were heated to 170° F. Similarly, the ingredients in the water phase were heated to the same temperature. The isethionate was added to the oil phase and homogenized into it using a relatively low level of agitation. The water phase was added to the oil phase and homogenized under similar conditions for about 10 minutes. Thereafter, the color additive was added and the mixture was homogenized for 20 minutes to produce a translucent water-in-oil emulsion.

In the Example given above, the emulsifier and surface active detergent were both added along with the other additives of the oil phase. It is to be understood, however, that when the oil and water phase materials are brought toqether, the detergent migrates into the water phase and the emulsifier represents a separate component responsible for the stability of the present water-in-oil emulsion.

EXAMPLE 2

This illustrates another embodiment of the present invention.

| Ingredient | Weight Percent |
| --- | --- |
| Petroleum Jelly | 50.00 |
| Mineral Oil | 10.00 |
| Polyglycerol isostearate (WITCONOL 18L) | 1.00 |
| Sodium cocoyl isethionate | 4.00 |
| Propylparaben | 0.10 |
| Sodium pyrrolidone carboxylic acid solution (50%) | 14.85 |
| Sugar | 12.47 |
| Methylparaben | 0.10 |
| Color | 0.05 |
| Water | 7.43 |

The formulation resulting from appropriate admixture (as described in Example 1) of the above ingredients showed good rinsability.

EXAMPLE 3

This Example illustrates the use of a combination of humectants to prepare a water-in-oil emulsion where the secondary humectant (glycerine) was present at well under 50% by weight of the humectant content.

| Ingredient | Weight Percent |
| --- | --- |
| Petroleum Jelly | 50.00 |
| Mineral Oil | 10.00 |
| Polyglycerol isostearate (WITCONOL 18L) | 1.00 |
| Propylparaben | 0.10 |
| Sodium cocoyl isethionate | 4.00 |
| Methylparaben | 0.10 |
| Sugar | 4.75 |
| Glycerine | 4.05 |
| Sodium pyrrolidone carboxylic acid solution (50% solution) | 24.00 |
| Water | 2.00 |

EXAMPLE 4

This illustrates another rinsable petroleum jelly formulation in accordance with the present invention.

| Ingredient | Weight Percent |
| --- | --- |
| Petroleum Jelly | 50.00 |
| Mineral Oil | 10.40 |
| Disodium salt of a substituted isopropanolamide half ester of sulfosuccinic acid (MONAMATE OPA-100) | 3.60 |
| Polyglycerol isostearate emulsifier | 1.00 |

| Ingredient | Weight Percent |
| --- | --- |
| Proplparaben | 0.10 |
| Sodium pyrrolidone carboxylic acid solution (50%) | 30.00 |
| Sugar | 4.80 |
| Methylparaben | 0.10 |

EXAMPLE 5

This is another rinsable petroleum jelly formulation using a sodium lauryl sulfoacetate-type surface active detergent.

| Ingredient | Weight Percent |
| --- | --- |
| Petroleum Jelly | 50.00 |
| Mineral Oil | 10.40 |
| Sodium lauryl sulfoacetate (LANTHANOL LAL) | 3.60 |
| Polyglycerol isostearate emulsifier | 1.00 |
| Propylparaben | 0.10 |
| Sodium pyrrolidone carboxylic acid solution (50%) | 30.00 |
| Sugar | 4.80 |
| Methylparaben | 0.10 |

EXAMPLE 6

The formulation described below formed an acceptable product illustrating the use of monosodium glutamate humectant in combination with sodium pyrrolidone carboxylic acid.

| Ingredient | Weight Percent |
| --- | --- |
| Petroleum Jelly | 50.00 |
| Mineral Oil | 10.00 |
| Sodium cocoyl isethionate | 4.00 |
| Monosodium glutamate | 4.80 |
| Polyglycerol isostearate | 1.00 |
| Sodium pyrrolidone carboxylic acid solution (50%) | 30.00 |
| Propylparaben | 0.10 |
| Methylparaben | 0.10 |

EXAMPLE 7

The five formulations described below were rinsable.

| | Weight Percent | | |
| --- | --- | --- | --- |
| Ingredient | A | B | C |
| Petroleum Jelly | 50.00 | 50.00 | 45.00 |
| Mineral Oil | — | 9.95 | 9.95 |
| Sodium cocoyl isethionate | 2.50 | 4.00 | 4.00 |
| Sugar | 8.25 | 5.00 | 5.00 |
| Urea | 8.25 | — | 5.00 |
| Polyglycerol isostearate | 1.00 | 1.00 | 1.00 |
| Yellow coloring | 0.05 | 0.05 | 0.05 |
| Sodium pyrrolidone carboxylic acid | 30.00 | 30.00 | 30.00 |

| | Weight Percent | |
| --- | --- | --- |
| Ingredient | D | E |
| Petroleum Jelly | 46.00 | 50.00 |
| Mineral Oil | 9.95 | 9.95 |
| Sodium cocoyl isethionate | 3.00 | — |
| Sugar | 5.00 | 5.00 |
| Urea | 5.00 | — |

-continued

| Ingredient | Weight Percent | |
|---|---|---|
| | D | E |
| Polyglycerol isostearate | 1.00 | 1.00 |
| Yellow coloring | 0.05 | 0.05 |
| Sodium pyrrolidone carboxylic acid | 30.00 | 30.00 |
| Sodium lauryl sulfate | — | 4.00 |

Of the formulations described above, B showed the most preferable equalities. Use of urea in formulations A, C and D might not be preferred in regard to commercial utility due to some discoloration which occurred on aging of the formulations.

COMPARATIVE EXAMPLE 8

This illustrates two incompatible formulations using sodium cocoyl glutamate as a surface active detergent in conjunction with sodium pyrrolidone carboxylic acid solution.

| Ingredient | Weight Percent | |
|---|---|---|
| | A | B |
| Petroleum Jelly | 50.00 | 50.00 |
| Mineral Oil | 10.00 | 11.00 |
| Sodium cocoyl isethionate | — | 2.00 |
| Sodium cocoyl glutamate | 4.00 | 1.00 |
| Polyglycerol isostearate emulsifier | 1.00 | 1.00 |
| Sugar | 5.00 | 5.00 |
| Sodium pyrrolidone carboxylic acid | 30.00 | 30.00 |

The resulting emulsions were grainy and cosmetically unacceptable.

EXAMPLE 9

Four additional formulations were made and tested.

| Ingredient | Weight Percent | |
|---|---|---|
| | A | B |
| Petroleum Jelly | 50.00 | 50.00 |
| Mineral Oil | 10.00 | 11.00 |
| Sodium cocoyl isethionate | 4.00 | 3.00 |
| Sugar | 5.00 | 5.00 |
| Polyglycerol isostearate | 1.00 | 1.00 |
| Sodium pyrrolidone carboxylic acid solution (50%) | 30.00 | 30.00 |
| | C | D |
| Petroleum Jelly | 50.00 | 50.00 |
| Mineral Oil | 12.00 | — |
| Sodium cocoyl isethionate | 2.00 | 2.00 |
| Sugar | 5.00 | 17.00 |
| Polyglycerol isostearate | 1.00 | 1.00 |
| Sodium pyrrolidone carboxylic acid solution (50%) | 30.00 | 30.00 |

Formulation A had good rinsability and was acceptable. Formulation B was more translucent than A but also rinsed very well. Formulation C exhibited somewhat less than preferred rinsability. Formulation D was similar to B but was somewhat more tacky or sticky in consistency.

Formulation A was judged to be the most superior.

EXAMPLE 10

The following formulation utilizes a taurate detergent rather than sodium cocoyl isethionate.

| Ingredients | Parts by Weight |
|---|---|
| Phase A | |
| Petroleum jelly | 50.0 |
| Mineral Oil | 10.5 |
| Polyglycerol isostearate | 1.0 |
| Coco-amide sulfonate (TAURANOL WS) | 4.8 |
| Propylparaben | 0.1 |
| Phase B | |
| Sodium pyrrolidone carboxylic acid solution | 30.0 |
| Sucrose | 4.5 |
| Methylparaben | 0.1 |

The resulting composition was very white and thickened at a relatively high temperature. It had comparable opaqueness to the compositions comprising sodium cocoyl isethionate, had comparable emulsion texture, and had comparable rinsability.

The foregoing Examples should not be construed in a limiting sense since they are merely presented to be illustrative of certain embodiments of the present invention. The claims which follow set forth the scope of protection desired.

We claim:

1. A water rinsable petroleum jelly water-in-oil emulsion, containing a predominant amount of a petroleum jelly component, comprising:
    (a) an aqueous phase comprising water a humectant and a surface active detergent effective to confer rinsable characteristics on the emulsion;
    (b) an oil phase comprising the predominating petroleum jelly component; and
    (c) a water-in-oil emulsifying agent.

2. An emulsion as claimed in claim which is translucent having essentially the same reflective index for its aqueous and oil phases.

3. an emulsion as claimed in claim 1 wherein the humectant comprises a mixture of humectants in the aqueous phase.

4. An emulsion as claimed in claim 1 wherein the oil phase ranges from about 40% to about 70%, by weight of the emulsion.

5. An emulsion as claimed in claim 1 wherein the aqueous phase ranges from about 30% to about 60% by weight of the emulsion.

6. An emulsion as claimed in claim 1 wherein the surface active detergent is selected from the group consisting of the amido sulfonates, the 2-sulfoethyl esters of fatty acids, the alkali metal alkyl sulfates, the alkali metal alkyl sulfoacetates, the alkali metal sulfosuccinate esters of modified alkanolamines, and the dialkyl alkali sulfosuccinates.

7. An emulsion as claimed in claim 1 which comprises the sodium salt of pyrrolidone carboxylic acid as a humectant in the aqueous phase and which has essentially the same refractive index for the aqueous and oil phases to yield a translucent composition.

8. An emulsion as claimed in claim 7 wherein the oil phase ranges from about 40% to about 70%, the aqueous phase ranges from about 30% to about 60%, and the amount of water-in-oil emulsifier ranges from about 0.1% to about 5%, all amounts based on the weight of the emulsion.

9. An emulsion as claimed in claim 8 wherein the amount of water ranges from about 6% to about 20% by weight of the emulsion.

10. An emulsion as claimed in claim 1 wherein the amount of water ranges from about 6% to about 20% by weight of the emulsion.

11. A translucent, water rinseable petroleum jelly water-in-oil emulsion containing a predominant amount of a petroleum jelly component comprising:
(a) an aqueous phase comprising a humectant and sodium cocoyl isethionate as a surface active detergent effective to confer rinsable characteristics on the emulsion;
(b) an oil phase comprising the predominating petroleum jelly component; and
(c) a water-in-oil emulsifying agent.

12. An emulsion of claim 11 which comprises the sodium salt of pyrolidone carboxylic acid as a humectant in the aqueous phase and which has essentially the same refractive index for the aqueous and oil phases to provide a translucent composition.

13. A water rinsable petroleum jelly water-in-oil emulsion comprising:
(a) an aqueous phase comprising a humectant and sodium cocoyl isethionate as a surface active detergent effective to confer rinsable characteristics on the emulsion;
(b) an oil phase comprising a petroleum jelly component; and
(c) a water-in-oil emulsifying agent.

14. A water rinsable petroleum jelly water-in-oil emulsion, with its aqueous and oil phases having essentially the same refractive index to yield a translucent composition, comprising:
(a) an aqueous phase comprising the sodium salt of pyrrolidone carboxylic acid as a humectant and sodium cocoyl isethionate as a surface active detergent effective to confer rinsable characteristics on the emulsion;
(b) an oil phase comprising a petroleum jelly component; and
(c) a water-in-oil emulsifying agent.

15. A water rinsable petroleum jelly water-in-oil emulsion, with its aqueous and oil phases having essentially the same refractive index to yield a translucent composition, comprising:
(a) from about 30% to about 60% by weight, of an aqueous phase comprising the sodium salt of pyrrolidone carboxylic acid as a humectant and sodium cocoyl isethionate as a surface active detergent effective to confer rinsable characteristics on the emulsion;
(b) from about 40% to about 70%, by weight, of an oil phase comprising a petroleum jelly component; and
(c) from about 0.1% to about 5%, by weight, of a water-in-oil emulsifying agent.

16. A water rinsable petroleum jelly water-in-oil emulsion comprising:
(a) from about 40% to about 70% by weight of the petroleum jelly component;
(b) from about 30% to about 60% by weight of an aqueous phase comprising a humectant;
(c) from about 0.1% to about 5% by weight of a fatty acid ester of polyglycerol emulsifying agent; and
(d) from about 2% to about 8% by weight of at least one surface active detergent selected from the group consisting of amido sulfonates, 2-sulfoethyl esters of fatty acids, alkali metal alkyl sulfates, alkali metal alkyl sulfoacetates, alkali metal sulfosuccinate esters of alkalolamines, and dialkyl alkali metal sulfosuccinates.

17. A water rinsable petroleum jelly water-in-oil emulsion of claim 16 wherein the emulsion contains from about 6% to about 20% by weight of water.

18. A water rinsable petroleum jelly water-in-oil emulsion of claim 16 wherein the emulsion contains from about 10% to about 20% by weight of humectant, based on the weight of the emulsion, in the aqueous phase.

* * * * *